United States Patent
Govari et al.

(10) Patent No.: US 10,492,854 B2
(45) Date of Patent: Dec. 3, 2019

(54) CATHETER-BASED ACOUSTIC RADIATION FORCE IMPULSE SYSTEM

(75) Inventors: Assaf Govari, Haifa (IL); Andres Claudio, Haifa (IL); Gilad Adler, Haifa (IL)

(73) Assignee: BIOSENSE WEBSTER, INC., Diamond Bar, CA (US)

( * ) Notice: Subject to any disclaimer, the term of this patent is extended or adjusted under 35 U.S.C. 154(b) by 1205 days.

(21) Appl. No.: 11/950,946

(22) Filed: Dec. 5, 2007

(65) Prior Publication Data

US 2009/0149753 A1    Jun. 11, 2009

(51) Int. Cl.
*A61B 18/14*    (2006.01)

(52) U.S. Cl.
CPC .................. *A61B 18/1492* (2013.01)

(58) Field of Classification Search
USPC ....................... 600/437–439, 462–467; 601/2
See application file for complete search history.

(56) References Cited

U.S. PATENT DOCUMENTS

| | | | |
|---|---|---|---|
| 2,645,386 A | 7/1953 | Bobrick | |
| 5,471,988 A | 12/1995 | Fujio et al. | |
| 5,669,389 A * | 9/1997 | Rotteveel et al. | 600/459 |
| 5,893,848 A | 4/1999 | Negus et al. | |
| 6,332,089 B1 | 12/2001 | Acker et al. | |
| 6,371,912 B1 | 4/2002 | Nightingale et al. | |
| 6,618,612 B1 | 9/2003 | Acker et al. | |
| 6,658,279 B2 | 12/2003 | Swanson et al. | |
| 6,690,963 B2 | 2/2004 | Ben-Haim et al. | |
| 2002/0065455 A1 | 5/2002 | Ben-Haim et al. | |
| 2003/0130657 A1* | 7/2003 | Tom | A61B 8/06 606/47 |
| 2004/0068178 A1 | 4/2004 | Govari | |
| 2004/0147920 A1 | 7/2004 | Keidar | |
| 2005/0215899 A1 | 9/2005 | Trahey et al. | |
| 2006/0079773 A1* | 4/2006 | Mourad et al. | 600/438 |
| 2007/0073135 A1 | 3/2007 | Lee | |
| 2007/0129633 A1 | 6/2007 | Lee et al. | |
| 2009/0149753 A1 | 6/2009 | Govari et al. | |

FOREIGN PATENT DOCUMENTS

| | | |
|---|---|---|
| EP | 1 554 986 A | 7/2005 |
| EP | 2067446 A1 | 6/2009 |
| JP | 1993-228150 A | 8/1993 |
| JP | 2002-516586 | 6/2002 |
| JP | 2005-532097 | 6/2002 |

(Continued)

OTHER PUBLICATIONS

Sugimoto et al., "Tissue Hardness Measurment using the Radiation Force of Focused Ultrasound", IEEE Ultrasonics Symposium, 1990.*

(Continued)

*Primary Examiner* — Christopher L Cook
(74) *Attorney, Agent, or Firm* — Notaro, Michalos & Zaccaria P.C.

(57) ABSTRACT

A probe, including an ablation element which is configured to perform ablation of tissue. The probe also includes an ultrasonic transducer, located in proximity to the ablation element, which is configured to transmit acoustic radiation force impulses (ARFIs) to the tissue, and to measure a displacement of the tissue in response to the ARFIs so as to monitor the ablation of the tissue.

35 Claims, 10 Drawing Sheets

(56) References Cited

FOREIGN PATENT DOCUMENTS

| JP | 2005-199072 | 7/2005 |
|---|---|---|
| JP | 2007-152094 | 6/2007 |
| JP | 2007-227395 | 9/2007 |
| WO | WO 04/002305 A2 | 1/2004 |
| WO | WO 2008/112005 A | 9/2008 |

OTHER PUBLICATIONS

De Silva, Clarence W., "Mechatronics: An Integrated Approach", 2005, pp. 596-597.*
Citation: de Silva, Clarence, W., Mechatronics: An Integrated Approach, Nov. 29, 2004.*
Fahey, Brian J. et al. Acoustic Radiation Force Impulse Imaging of Myocardial Radiofrequency Ablation: Initial in Vivo Results, IEEE Transactions on Ultrasonics, Ferroelectrics, and Frequency Control, vol. 52, No. 4, Apr. 2005, pp. 631-641.
Hsu, Stephen J. et al. In Vivo Assessment of Myocardial Stiffness With Acoustic Radiation Force Impulse Imaging, Ultrasound in Medicine & Biology, vol. 33, Issue 11, Nov. 2007, pp. 1706-1719.
Wolf, Patrick D. Ultrasound Based Multimodal Imaging System for Guiding Cardiac Ablation Therapy, Duke University Project, Aug. 1, 2007-Jul. 31, 2010. Abstract.
Fahey, B.J et al.; ARFI Imaging of Thermal Lesions in Ex Vivo and In Vivo Soft Tissues, IEEE 1992 Ultrasonics Symposium: vol. 1, pp. 562-567, 2003.
Hsu S.J. et al. Invivo acoustic radiation force impulse imaging of cardiac ablations: Proceedings—IEEE Ultrasonics Symposium—2005 Institute of Electrical and Electronics Engineers Ins. US vol. 2, 2004, pp. 1117-1121.
EP Partial Search Report No. EP 08 25 3876 dated Mar. 24, 2009.
JP Office Action, JP No. 2008-309216 dated Jul. 10, 2013.
JP Office Action, JP No. 2008-309216 dated Apr. 16, 2013.
Canadian Search Report, Application No. 2,645,386 dated Jan. 9, 2017.
De Silva, C.W., Mechatronics: An Integrated Approach, Jul. 15, 2004.
First Examination Report from Intellectual Property India for corresponding Indian Application No. 2015/KOL/2008.
Canadian Examination Report for corresponding Canadian application No. CA 2,645,386, dated Sep. 28, 2018.

\* cited by examiner

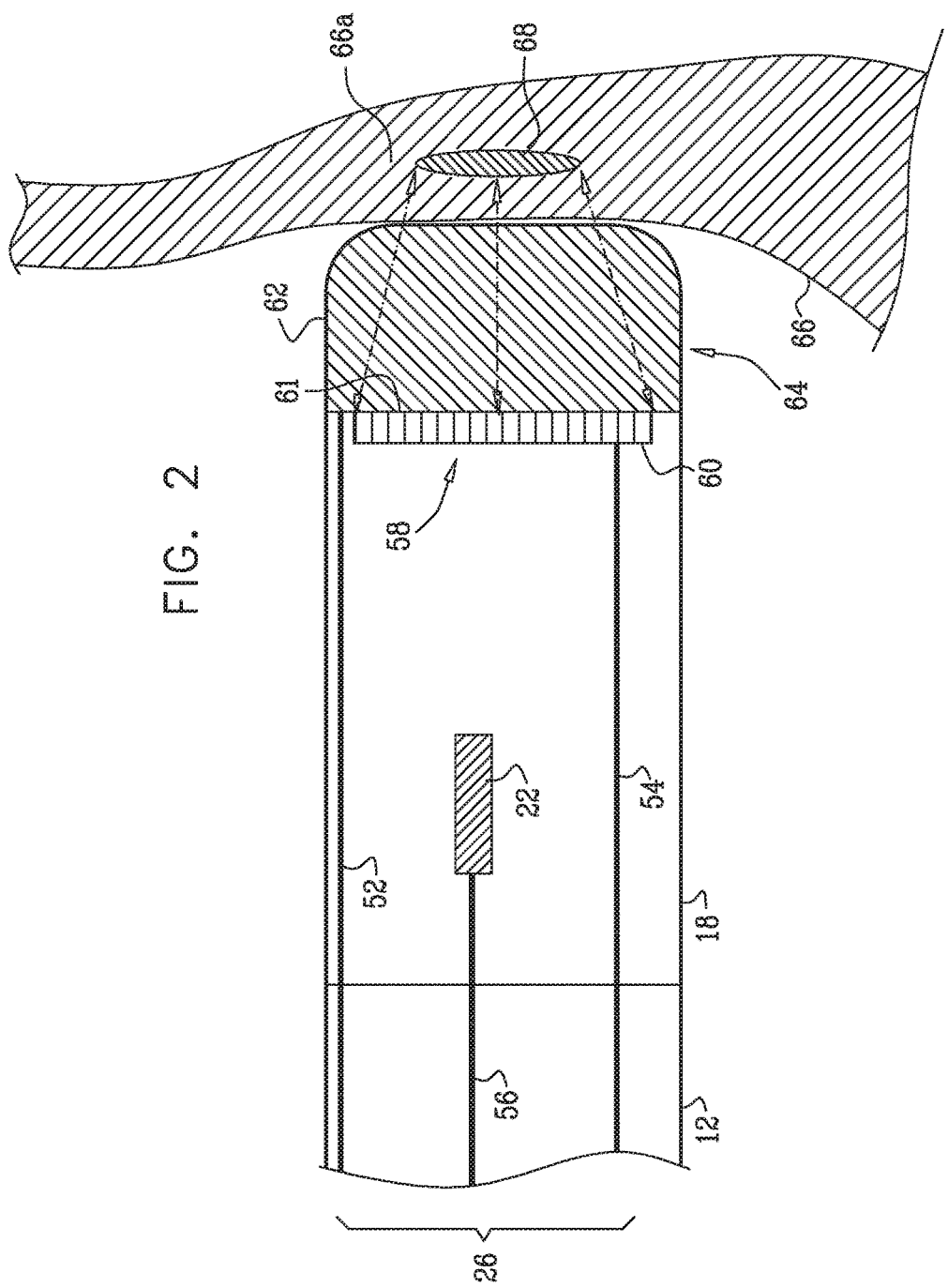

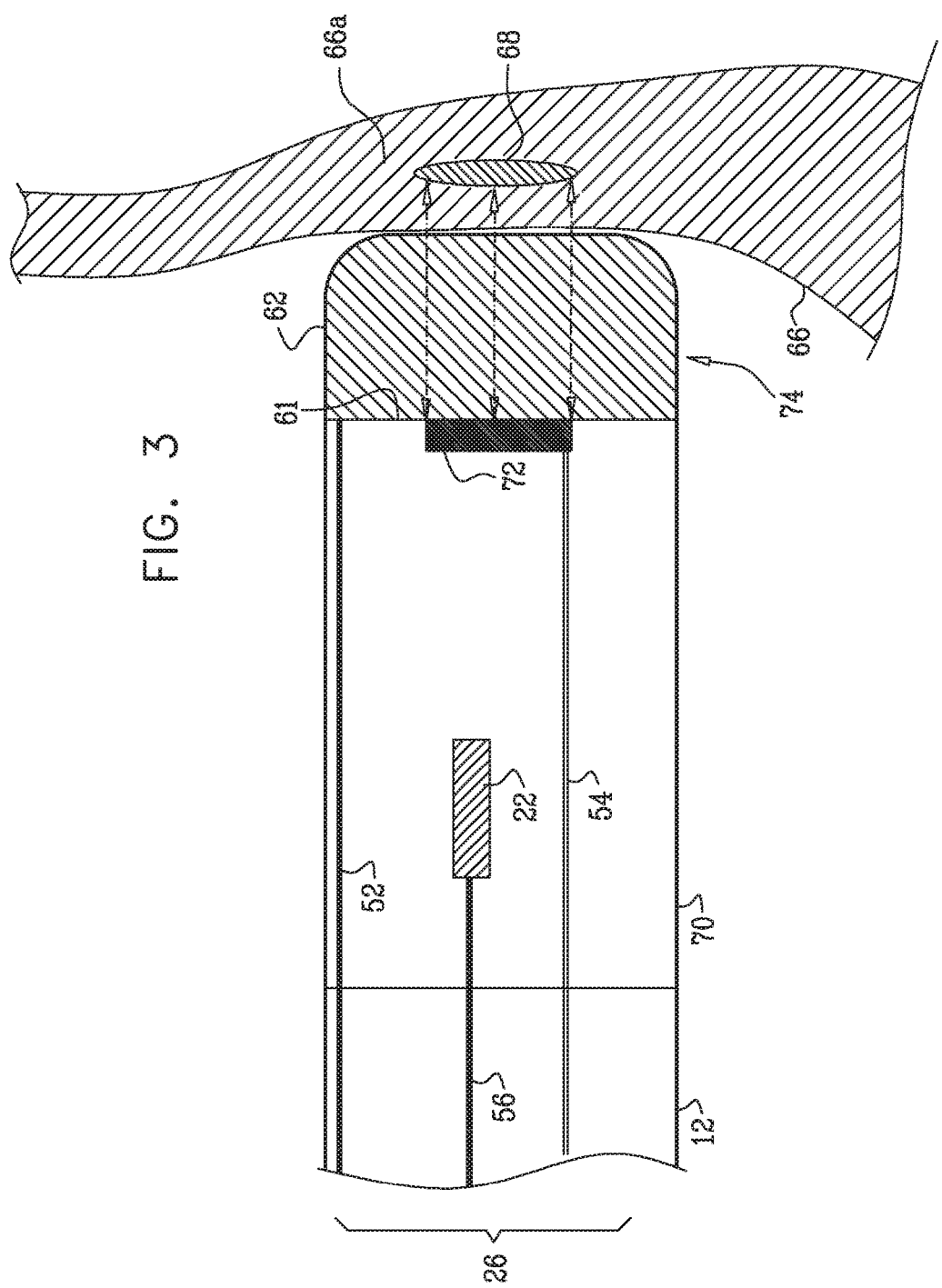

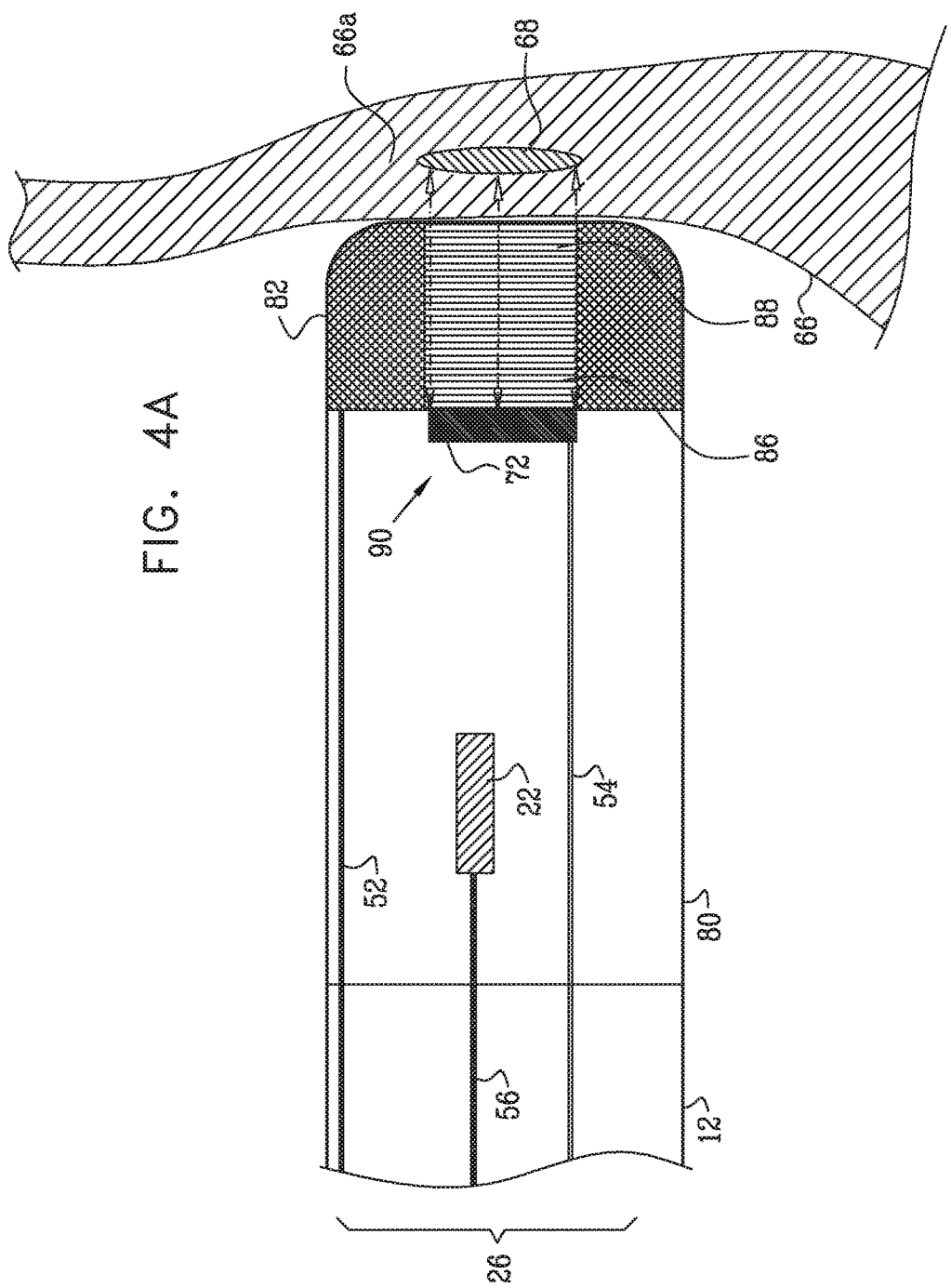

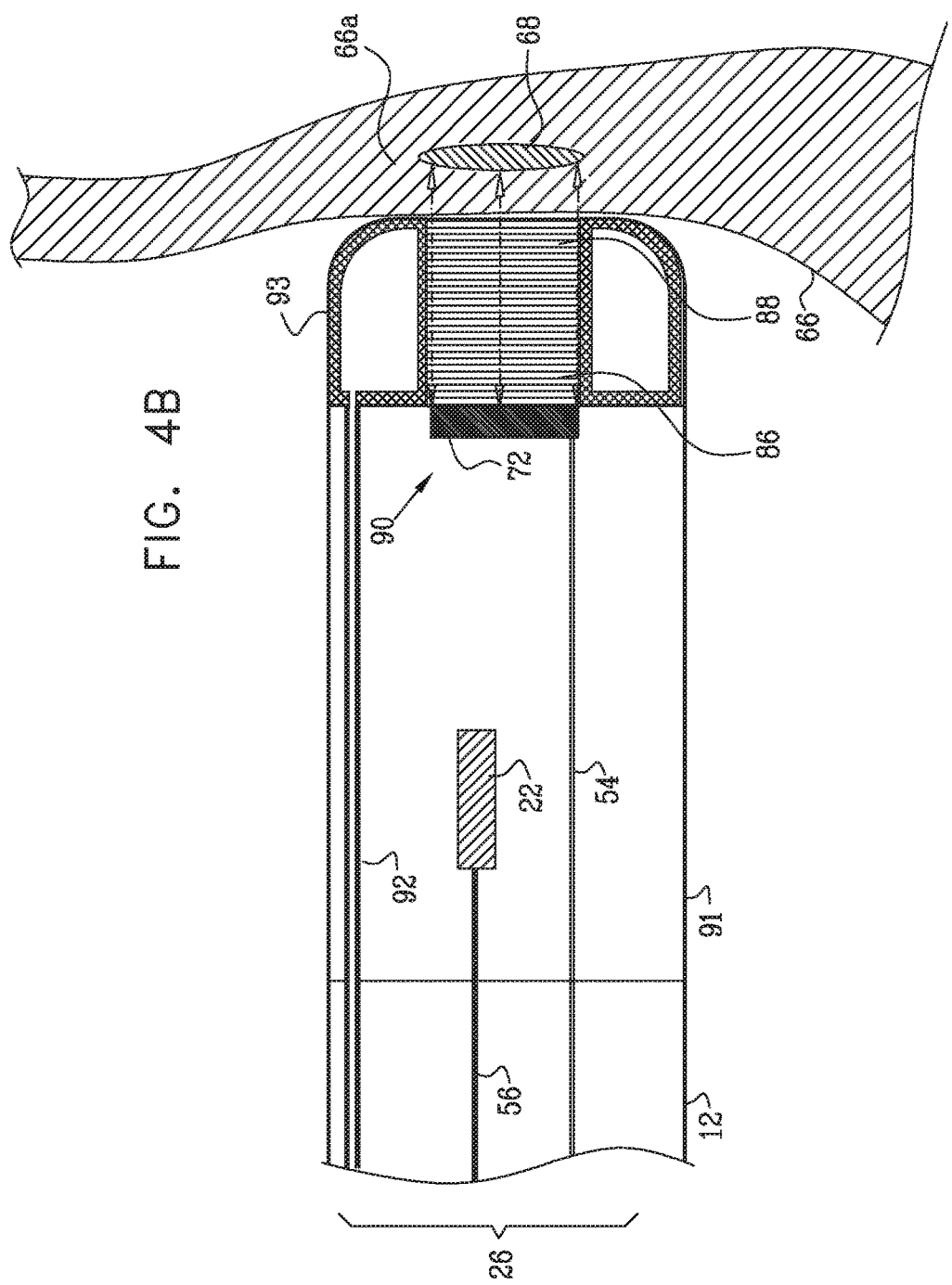

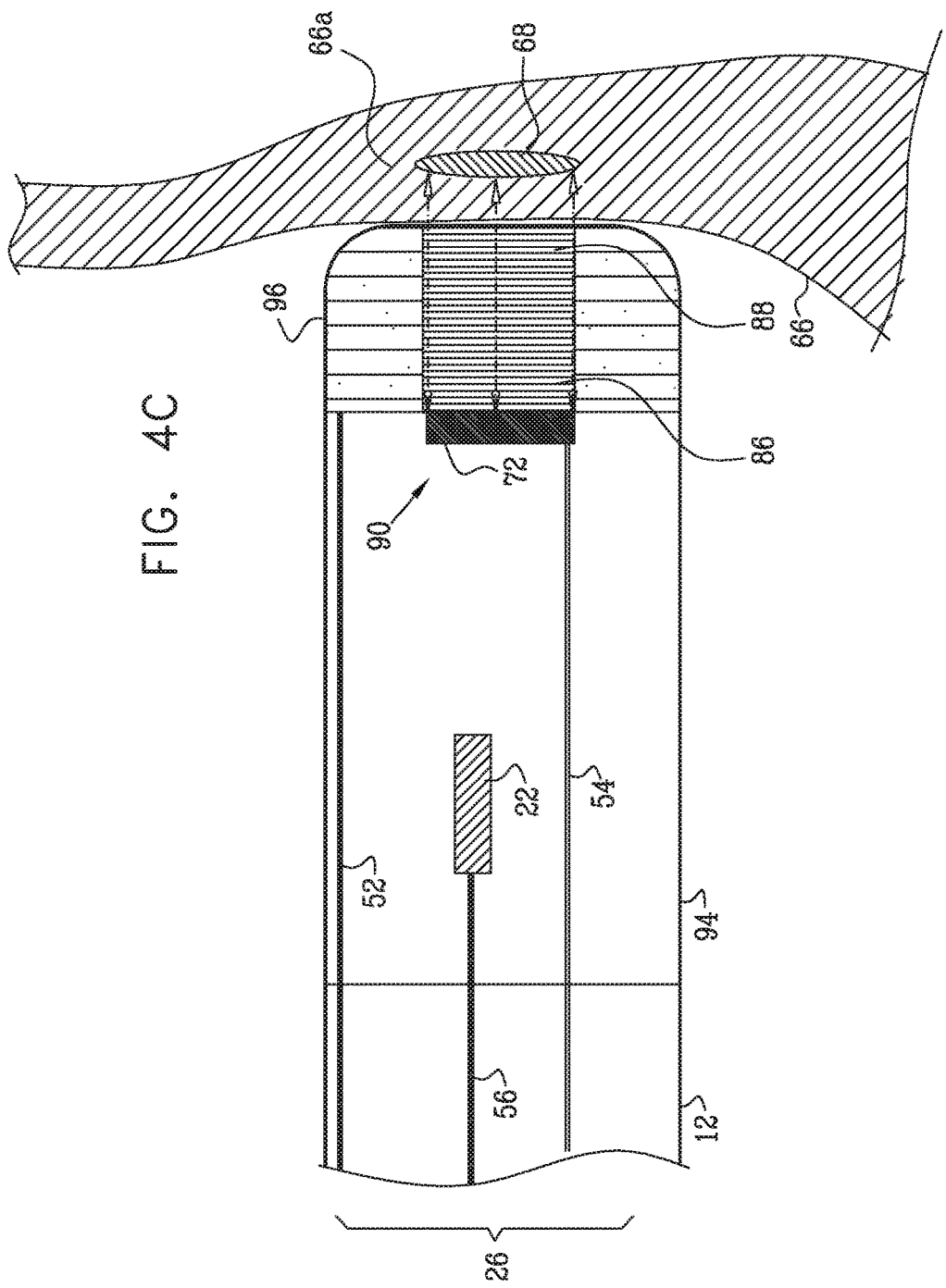

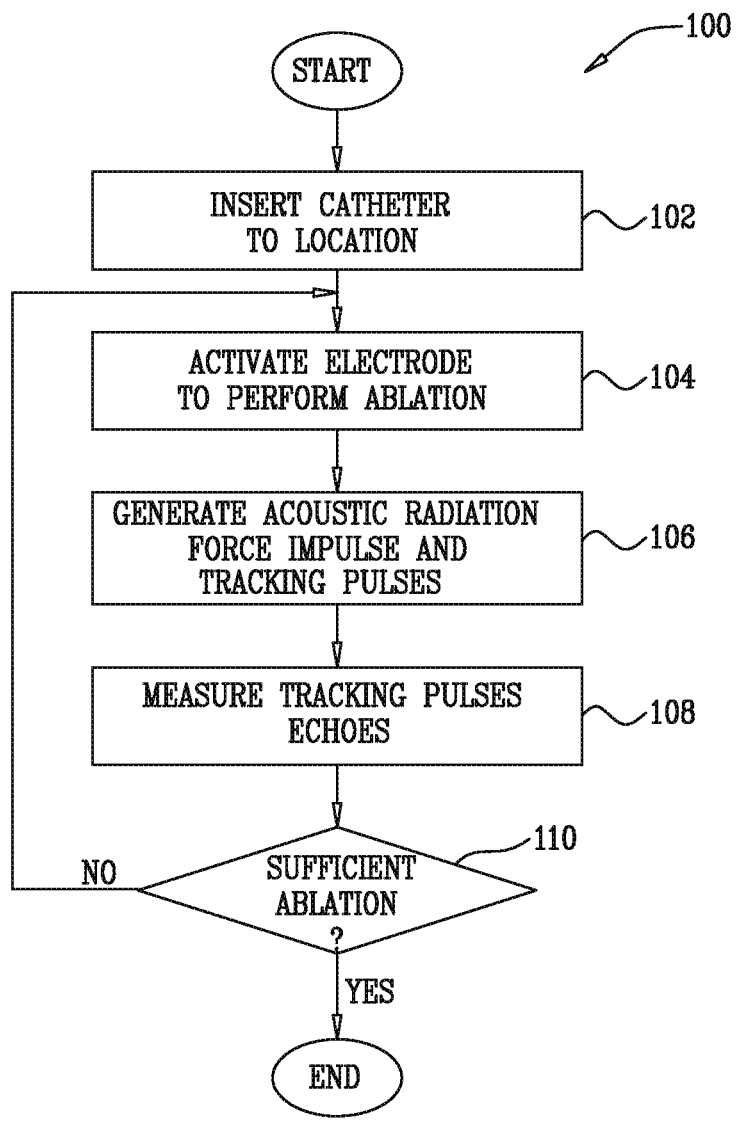

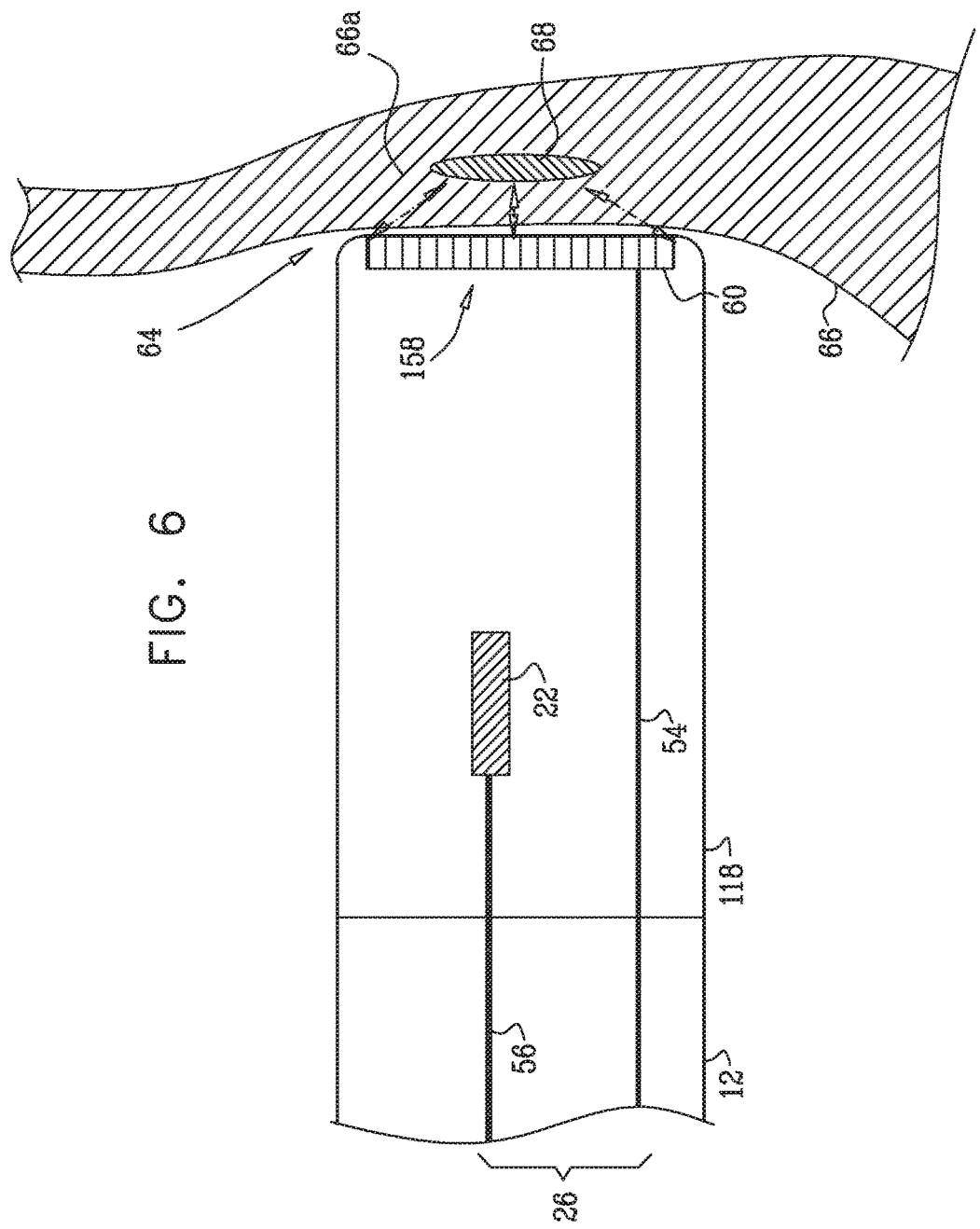

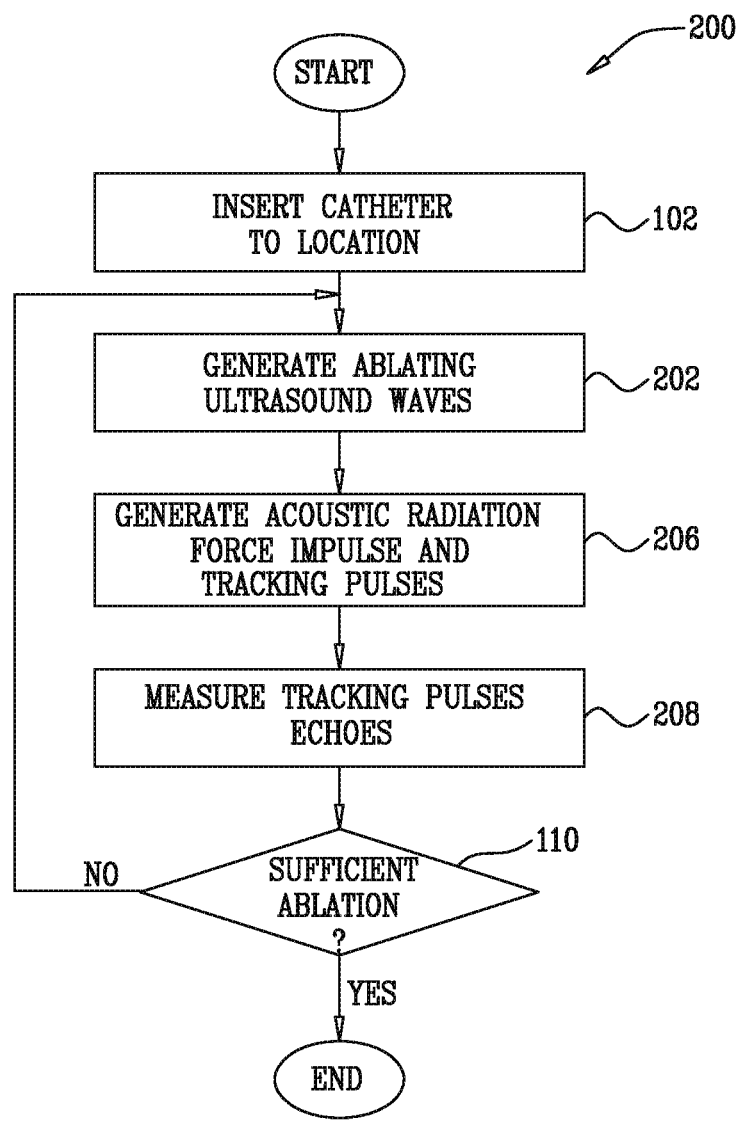

CATHETER-BASED ACOUSTIC RADIATION FORCE IMPULSE SYSTEM

FIELD OF THE INVENTION

The present invention relates generally to ultrasonic systems, and particularly to ultrasonic systems used for medical procedures.

BACKGROUND OF THE INVENTION

An article of The Ultrasonic Imaging Laboratory in the Joint University of North Carolina at Chapel Hill, N.C. State University Department of Biomedical Engineering, which may be found at www.bme.ncsu.edu/labs/ULSlab/index.html, explains Acoustic radiation force impulse (ARFI) imaging. The article is incorporated herein by reference. The article states that "in ARFI imaging, an impulse of relative high acoustic energy is transmitted into the body to deliver spatially and temporally localized radiation force at the imaging focus in a manner that subtly pushes tissue away from the imaging transducer (tissue displacement is on the order of microns). Each ARFI impulse is followed by ensembles of conventional ultrasonic transmit-receive lines, which serve to generate data for ARFI-induced axial motion tracking with one-dimensional cross-correlation. Displacements measured in space and time may then be rendered into graphical and parametric image representations that depict differences in tissue mechanical properties."

Some of the references cited below give more detail of ARFIs.

In an article entitled "Acoustic radiation force impulse imaging of myocardial radio-frequency ablation: initial in vivo results" by Fahey et al., published in IEEE Transactions on Ultrasonics, Ferroelectrics and Frequency Control, Volume 52, Issue 4, April 2005 Page(s): 631-641, the authors state that "Acoustic radiation force impulse (ARFI) imaging techniques were used to monitor radio-frequency (RF) ablation of ovine cardiac tissue in vivo." The article is incorporated herein by reference.

In an article entitled "ARFI imaging of thermal lesions in ex vivo and in vivo soft tissues" by Fahey at al., published in the IEEE Symposium on Ultrasonics, 2003 Volume 1, pages 562-567, which is incorporated herein by reference, the authors state that "the ability of ARFI imaging to monitor the ablation of soft tissues both ex vivo and in vivo was investigated."

U.S. Patent Application 20040147920 to Keidar, which is incorporated herein by reference, describes how ultrasound measurement may be used in assessment of ablation.

U.S. Pat. No. 6,658,279 to Swanson et al., which is incorporated herein by reference, describes a catheter for ablating and imaging tissue. The catheter includes a porous electrode.

U.S. Pat. No. 6,371,912 to Nightingale et al., which is incorporated herein by reference, describes a method and apparatus for the identification and characterization of regions of altered stiffness.summary of the invention In an embodiment of the present invention, a probe positioned at the distal end of a catheter is used to perform ablation of tissue. The probe is also able to monitor the ablation. To perform the two functions, the probe comprises an ablation element and an ultrasonic transducer, mounted in proximity to each other. To monitor the ablation, the ultrasonic transducer is configured to transmit acoustic radiation force impulses (ARFIs) via, or in proximity to, the element to the ablated tissue. The impulses displace the tissue by an amount that depends on the elasticity of the tissue, and the transducer is also able to measure the displacement of the tissue. Since ablated and non-ablated tissues have different elasticities, the different displacements enable the ablation of the tissue to be monitored. By incorporating the ablation element and the transducer into the one probe, there is no need for a second ultrasonic device separate from the probe. Furthermore, since the ultrasonic transducer is close to the site of ablation, the ablation may be monitored more accurately and lower ultrasonic energies may be used, while still achieving comparable results to those of external transducers.

In some embodiments the ablation element comprises a radio-frequency (RF) electrode which is typically a sonolucent electrode. The transducer is mounted in acoustic contact with the electrode and the mounting is such that forward ultrasound waves generated by the transducer, as well as returning ultrasonic waves, traverse the electrode without appreciable reflection. The ultrasound waves that traverse the electrode comprise ARFIs, ultrasonic tracking pulses, and tracking pulse reflections used to monitor the displacement of the tissue due to the ARFIs. Alternatively or additionally, the electrode comprises an acoustically transparent aperture. The transducer is mounted so that the ultrasound waves described above travel through the electrode via the aperture.

In alternative disclosed embodiments the ablation element ablates cryogenically, or uses microwaves to perform the ablation.

In a further alternative embodiment, rather than the tissue ablation being performed using a separate ablation element, the tissue is ablated by ultrasound. In this case the ultrasonic transducer may be used to perform the ablation by radiating ablating ultrasound, and there is no need for a separate ablation element in the probe.

There is therefore provided, according to an embodiment of the present invention, a probe, including:

an ablation element which is configured to perform ablation of tissue; and an ultrasonic transducer, located in proximity to the ablation element, which is configured to transmit acoustic radiation force impulses (ARFIs) to the tissue, and to measure a displacement of the tissue in response to the ARFIs so as to monitor the ablation thereof.

In an embodiment, the ablation element includes an aperture, and the ultrasonic transducer is configured to direct the ARFIs to the tissue via the aperture. The probe may include a good acoustic transmission medium which fills the aperture.

In a disclosed embodiment the ultrasonic transducer includes an array of transducer elements. The array may be configured to focus the ARFIs onto the tissue. Alternatively or additionally the array may be configured to generate an image of the tissue.

Typically, the ablation element includes an electrode configured to perform radio-frequency (RF) ablation of the tissue. In an embodiment, the electrode includes a sonolucent electrode, and the transducer is configured to transmit the ARFIs in response to receipt of electrical radio-frequency (RF) ARFI signals, to transmit ultrasonic tracking pulses via the sonolucent electrode to the tissue in response to receipt of electrical RF tracking pulses, to receive respective reflections of the ultrasonic tracking pulses from the tissue via the sonolucent electrode, and to generate electrical RF reflection pulses in response to the reflections. The probe may include a processor which is configured to convey the electrical RF ARFI pulses and the electrical RF tracking pulses to the transducer, and to receive the electrical RF reflection pulses from the transducer so as to measure the displacement of the tissue.

In a disclosed embodiment the ablation element includes a cooling element configured to perform cryogenic ablation of the tissue.

In an alternative disclosed embodiment the ablation element includes a microwave radiator configured to perform microwave ablation of the tissue.

There is further provided, according to an embodiment of the present invention, apparatus for ablating tissue, including:

a probe including an array of ultrasonic transducer elements which is configured to direct ultrasonic waves to the tissue in response to an electrical radio-frequency (RF) signal, and to receive reflected ultrasonic waves from the tissue; and an RF transceiver, which:

in a first transceiver state is configured to convey an electrical ablating RF signal to the array causing the array to transmit ablation ultrasonic pulses to the tissue, the ablation ultrasonic pulses having an energy sufficient to cause ablation of the tissue, in a second transceiver state is configured to convey an electrical acoustic radiation force impulse (ARFI) RF signal to the array causing the array to transmit an ARFI to the tissue, and in a third transceiver state is configured:

to convey an electrical tracking RF signal to the array causing the array to transmit one or more tracking ultrasonic pulses to the tissue, to receive electrical RF reflection signals from the array generated in response to the array receiving reflections of the one or more tracking ultrasonic pulses from the tissue, and to measure a displacement of the tissue in response to the electrical RF reflection signals, so as to monitor the ablation of the tissue.

Typically, the RF transceiver is configured in a fourth transceiver state to convey an electrical imaging RF signal to the array causing the array to transmit one or more imaging ultrasonic pulses to the tissue, and to receive electrical RF imaging reflection signals from the array generated in response to the array receiving reflections of the one or more imaging ultrasonic pulses from the tissue.

There is further provided, according to an embodiment of the present invention, a method for ablating tissue, including:

providing an ablation element;

performing ablation of the tissue using the ablation element;

locating an ultrasonic transducer in proximity to the ablation element;

transmitting acoustic radiation force impulses (ARFIs) from the transducer to the tissue; and measuring a displacement of the tissue in response to the ARFIs so as to monitor the ablation thereof.

There is further provided, according to an embodiment of the present invention, a method for ablating tissue, including:

configuring a probe comprising an array of ultrasonic transducer elements to direct ultrasonic waves to the tissue in response to an electrical radio-frequency (RF) signal, and to receive reflected ultrasonic waves from the tissue; and providing an RF transceiver, which:

in a first transceiver state is configured to convey an electrical ablating RF signal to the array causing the array to transmit ablation ultrasonic pulses to the tissue, the ablation ultrasonic pulses having an energy sufficient to cause ablation of the tissue, in a second transceiver state is configured to convey an electrical acoustic radiation force impulse (ARFI) RF signal to the array causing the array to transmit an ARFI to the tissue, and in a third transceiver state is configured:

to convey an electrical tracking RF signal to the array causing the array to transmit one or more tracking ultrasonic pulses to the tissue, to receive electrical RF reflection signals from the array generated in response to the array receiving reflections of the one or more tracking ultrasonic pulses from the tissue, and to measure a displacement of the tissue in response to the electrical RF reflection signals, so as to monitor the ablation of the tissue.

The present invention will be more fully understood from the following detailed description of the embodiments thereof, taken together with the drawings in which:

BRIEF DESCRIPTION OF THE DRAWINGS

FIG. 2 is a schematic diagram of a probe used in the system of FIG. 1, according to an embodiment of the present invention;

FIG. 3 is a schematic diagram of a probe used in the system of FIG. 1, according to an alternative embodiment of the present invention;

FIGS. 4A, 4B, and 4C are schematic diagrams of probes used in the system of FIG. 1, according to further alternative embodiments of the present invention;

FIG. 5 is a flowchart showing steps involved in operating the system of FIG. 1, according to an embodiment of the present invention;

FIG. 6 is a schematic diagram of a probe used in ablating tissue, according to a yet further alternative embodiment of the present invention;

FIG. 8 is a flowchart showing steps involved in operating the system of FIG. 7, according to an embodiment of the present invention.

DETAILED DESCRIPTION OF EMBODIMENTS

Figure 1:
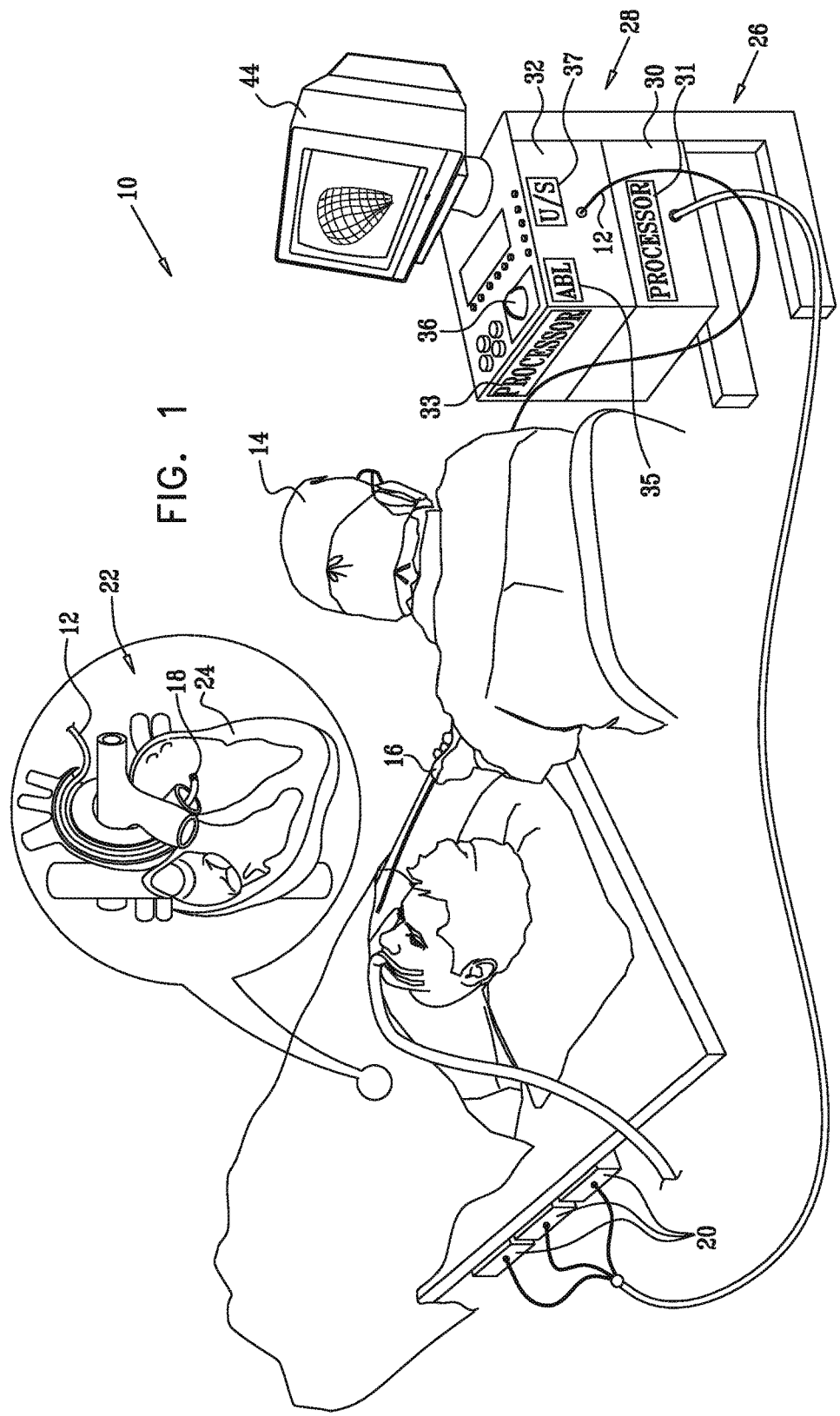
FIG. 1 is a schematic, pictorial illustration of a system for ablating tissue of a patient, according to an embodiment of the present invention.

Reference is now made to FIG. 1, which is a schematic, pictorial illustration of a system 10 for ablating tissue of a patient, according to an embodiment of the present invention. System 10 may be used to ablate tissue in different organs of a patient, and herein, by way of example, the ablated tissue is assumed to be comprised in the heart 24 of the patient. System 10 comprises a catheter 12, which is inserted by a physician 14 into a chamber of the heart through a vein or artery. Catheter 12 typically comprises a handle 16 for operation of the catheter by the physician. Suitable controls on the handle enable the physician to steer, position and orient a probe 18, mounted on the distal end of the catheter, as desired. System 10 typically comprises a positioning sub-system that measures location and orientation coordinates of probe 18.

In one embodiment, the positioning sub-system comprises a magnetic position tracking system that determines the position and orientation of probe 18. The positioning sub-system generates magnetic fields in a predefined working volume and senses these fields at the probe. The positioning sub-system typically comprises a set of external radiators, such as field generating coils 20, which are located in fixed, known positions external to the patient. Coils 20 generate fields, typically magnetic fields, in the vicinity of heart 24. The generated fields are sensed by a position sensor 22 in probe 18. Probe 18 is shown in more detail in FIG. 2.

In an alternative embodiment, a radiator in the probe, such as a coil, generates magnetic fields. The fields are received by sensors outside the patient's body.

Position sensor 22 transmits, in response to the sensed fields, position-related electrical signals over cabling 26 running through the catheter to a console 28. Alternatively, the position sensor may transmit signals to the console over a wireless link. The console comprises a positioning module 30, operated by a positioning processor 31, which controls the magnetic fields referred to above. Module 30 calculates the location and orientation of probe 18 based on the signals sent by position sensor 22. In order to perform its calculations, positioning module 30 typically receives, amplifies, filters, digitizes, and otherwise processes signals from sensor 22.

Some position tracking systems that may be used in system 10 are described, for example, in U.S. Pat. Nos. 6,690,963, 6,618,612 and 6,332,089, and U.S. Patent Application Publications 2002/0065455 A1, 2004/0147920 A1 and 2004/0068178 A1, whose disclosures are all incorporated herein by reference. Although the positioning sub-system shown in FIG. 1 uses magnetic fields, any other suitable positioning sub-system, such as systems based on electromagnetic fields, acoustic or ultrasonic measurements, may be used.

System 10 also comprises an ablation module 32, operated by an ablation processor 33. Except where stated herein, ablation module 32 operates as a transceiver, and may be referred to herein as transceiver module 32. Transceiver module 32 transmits electrical signals to, and receives electrical signals from, probe 18 via cabling 26. The signals transferred, and the functions performed by transceiver module 32, are described in more detail below. A display 44 provides physician 14 with a graphic user interface showing results from the operation of system 10, as well as allowing the physician to control the system, typically via a pointing device 36 such as a trackball. Herein it is assumed that system 10 may be configured to operate in an ablation mode or in a non-ablation mode, the two modes being selectable by the physician using device 36. In the ablation mode, system 10 implements a flowchart 100, described below with reference to FIG. 5. In the non-ablation mode, probe 18 does not ablate tissue and flowchart 100 is not implemented. Elements 35 and 37 in system 10 are described below.

FIG. 2 is a schematic diagram of probe 18, according to an embodiment of the present invention. Probe 18 is mounted on the distal end of catheter 12. In one embodiment, probe 18 has a diameter in a range between approximately 1 mm and approximately 2 mm, and a length in a range between approximately 5 mm and approximately 8 mm. The probe comprises position sensor 22, and an ultrasonic transducer 60 which is formed from an array 58 of individual transducing elements. Array 58 may be a one-dimensional or a two-dimensional array, and is configured to be a forward-looking ultrasonic transducer array. A sonolucent electrode 62 is mounted on catheter 12, on the distal side of, and in acoustic contact with, transducer 60. As described below, electrode 62 is configured as an ablation element. The electrode is typically mounted to be in direct physical contact with the elements of array 58. Alternatively, electrode 62 is separated from array 58 by a substantially non-reflective acoustically conductive material 61, such as hard plastic. Cabling 26 comprises separate cables 52, 54, and 56, which respectively connect with electrode 62, transducer 60, and sensor 22.

The physician is able to perform radio-frequency (RF) ablation of a section 68 of a tissue 66, by directing module 32, typically using pointing device 36 or handle 16, to send RF ablating signals via cable 52 to electrode 62. For example, tissue 66 may comprise a wall of the aorta of heart 24, and the physician desires to ablate section 68 of the wall. Using position sensor 22 the physician positions probe 18 to be substantially in contact with the section to be ablated, and directs the processor to generate the RF ablating signals. Transceiver module 32 comprises an ablation signal generator 35 which is assumed, except as described herein, to be an RF signal generator, and which processor 33 operates to generate the RF ablating signals. The signals are generated to have sufficient energy so that when they are applied to electrode 62, tissue ablation occurs.

The physician reviews the progress of the ablation by using array 58. Array 58 directs and focuses a set of one or more acoustic radiation force impulses (ARFIs), to tissue 66. Each ARFI typically comprises a focused ultrasonic pulse having a time period of the order of 30 μs. Transceiver module 32 comprises an RF ultrasonic signal generator 37 which is operated by processor 33 to generate electrical RF signals that are transferred to array 58 via cable 54 and that are used to power the elemental transducers of the array. To generate an ARFI, generator 37 directs RF pulses to each of the elemental transducers, the RF pulses having appropriate time delays so that a focused ultrasonic impulse, the ARFI, is produced by the array. Processor 33 may vary the time delays of the individual pulses to allow focusing of the impulse to be changed both in the direction of propagation of the impulse, and also laterally to the direction. Each set of ARFIs exerts a force on tissue 66 in the direction of travel of the ultrasonic pulses, and displaces the tissue by a displacement that is a function of the elasticity of the tissue.

To monitor the effect of the ARFIs on tissue, array 58 transmits ultrasonic tracking pulses, which may include pulses generated before, during, and after the set of ARFIs. The tracking pulses enable ablation processor 33 to measure the displacement caused by the ARFIs in both space and time. The displacement is evaluated by measuring the time of travel of the tracking pulses and their reflection from the tissue. Typically the time period of the tracking pulses is of the order of 0.2 μs. To generate the ultrasonic tracking pulses, processor 33 operates RF ultrasonic signal generator 37 to form appropriate electrical RF signals that are transferred to array 58 by cable 54. The reflections of the tracking pulses are received by array 58, which converts the reflected ultrasonic waves of the echoes to electrical RF signals that are transferred by cable 54 to processor 33.

From the measured displacements, an elasticity of tissue 66 may be calculated. Since the elasticity of unablated tissue "66a" is different from the elasticity of the ablated tissue, transceiver module 32 is able to use the difference to distinguish between ablated and unablated tissue "66a". If as explained below, array 58 images tissue 66, the difference may be used to show ablated tissue and unablated tissue "66a" in an image of the tissue presented on display 44.

As explained above, the ARFIs and the ultrasonic tracking pulses are both generated by array 58, and the impulses and tracking pulses transmit through sonolucent electrode 62 to tissue 66 without substantial reflection or loss of energy of the transmitted waves. Similarly, the reflections of the tracking pulses from the tissue traverse the electrode to array 58 without substantial change or loss of energy.

In addition to the functions described above, by virtue of the fact that transducer 60 comprises an array of elements, the array, together with processor 33, may be configured to form an ultrasonic image of tissue 66. In this case processor 33 directs an electrical imaging RF signal to the array causing the array to transmit one or more imaging ultrasonic pulses to the tissue. The processor receives electrical RF imaging reflection signals from the array, generated in response to the array receiving reflections of the imaging ultrasonic pulses, and forms an image of tissue 66 in response.

Processor 33 and array 58 thus operate together to perform four separate functions:
generation of ARFIs from RF signals
generation of ultrasonic tracking pulses from RF signals
conversion of reflections of the ultrasonic tracking pulses to RF signals
formation of an ultrasonic image.

Arrows 64 in FIG. 2 schematically illustrate paths and directions of ultrasonic waves that are generated for the four functions.

FIG. 3 is a schematic diagram of a probe 70, according to an embodiment of the present invention. Apart from the differences described below, the operation of probe 70 is generally similar to that of probe 18 (FIG. 2), and elements indicated by the same reference numerals in both probes 18 and 70 are generally similar in construction and in operation. In contrast to transducer 60 (probe 18) which is formed of an array of elements, probe 70 comprises an ultrasonic transducer 72 operating as a single ultrasonic element.

However, single element transducer 72, together with processor 33, may be configured to perform all the functions listed above for processor 33 and array 58, apart from forming an ultrasonic image. Thus, probe 70 may be used to perform tissue ablation, and track the progress of the ablation. The results may be presented on display 44, typically by overlaying color representing ablated and unablated tissue "66a" on an image of tissue 66 derived from an imaging source separate from probe 70, and/or by a graphical or numerical display on display 44, and/or by any other convenient system for displaying ablation produced by ARFIs.

FIG. 4A is a schematic diagram of a probe 80, according to an embodiment of the present invention. Apart from the differences described below, the operation of probe 80 is generally similar to that of probe 70 (FIG. 3), and elements indicated by the same reference numerals in both probes 70 and 80 are generally similar in construction and in operation.

Probe 80 comprises, instead of sonolucent electrode 62, an electrode 82 which has a central aperture 86 in the electrode. Electrode 82 acts as an ablation element, ablating tissue in a generally similar manner as electrode 62. Transducer 72 is mounted at the proximal end of the aperture, which is typically filled with a material 88, such as silicone, that is a good acoustic transmission medium. Thus, aperture 86 allows the ultrasonic waves of the ARFIs and the tracking pulses to be transmitted from the transducer via the electrode to tissue 66. Aperture 86 also allows reflections of the tracking pulses to be transmitted from tissue 66, via the electrode, to transducer 72.

Probe 80 performs the three functions described above for probe 70. The ablation performed by probe 80 may be tracked substantially as described above for probe 70.

In an alternative embodiment of probe 80, transducer 72 comprises an array 90 of transducing elements, generally similar to array 58 (FIG. 2). In this embodiment, probe 80 is able to perform the four functions described above for probe 18.

FIG. 4B is a schematic diagram of a probe 91, according to an embodiment of the present invention. Apart from the differences described below, the operation of probe 91 is generally similar to that of probes 70 and 80 (FIGS. 3 and 4A), and elements indicated by the same reference numerals in probes 70, 80, and 91 are generally similar in construction and in operation.

In contrast to probes 70 and 80, probe 91 performs ablation cryogenically, so that the ablation element of probe 91 comprises a cooling element 93. Element 93 is typically formed in the shape of a generally hollow toroid, the region at the center of the toroid, aperture 86, being filled by material 88. Element 93 receives cold gas, via a supply tube 92, from ablation module 32, and also exhausts the gas, via a tube not shown in FIG. 4B. The outer walls of element 93 thus cool and ablate tissue 66. However, it will be appreciated that probe 91 may comprise any other convenient cryogenic system for ablating tissue 66. For operating probe 91, module 32, in addition to being configured as a transceiver, also supplies cold gas, typically by evaporating liquid nitrogen, to tube 92.

Probe 91 performs the three functions described above for probe 70 and the ablation performed by probe 91 may be tracked substantially as described above for probe 70. In an alternative embodiment of probe 91, transducer 72 comprises an array 90 of transducing elements, generally similar to array 58 (FIG. 2). In this embodiment, probe 91 is able to perform the four functions described above for probe 18.

FIG. 4C is a schematic diagram of a probe 94, according to an embodiment of the present invention. Apart from the differences described below, the operation of probe 94 is generally similar to that of probes 70 and 80 (FIGS. 3 and 4A), and elements indicated by the same reference numerals in probes 70, 80, and 94 are generally similar in construction and in operation.

In contrast to probes 70 and 80, probe 94 performs ablation using microwave energy, so that the ablation element of probe 91 comprises a microwave radiator 96. Element 96 is typically formed in the shape of a toroid, the region at the center of the toroid, aperture 86, being filled by material 88. Element 96 receives microwave energy via cable 52 from ablation module 32. For operation of probe 94, ablation signal generator 35 in module 32 comprises a microwave generator. The generator typically operates at frequencies of the order of 2 GHz.

Probe 94 performs the three functions described above for probe 70 and the ablation performed by probe 94 may be tracked substantially as described above for probe 70. In an alternative embodiment of probe 94, transducer 72 comprises an array 90 of transducing elements, generally similar to array 58 (FIG. 2). In this embodiment, probe 94 is able to perform the four functions described above for probe 18.

FIG. 5 is a flowchart 100 showing steps involved in operating system 10, according to an embodiment of the present invention. In the following description of flowchart 100, it is assumed that physician 14 ablates section 68 of tissue 66 using probe 18 (FIGS. 1 and 2). Those having ordinary skill in the art will be able to adapt the description, mutatis mutandis, for other probes such as those described above with reference to FIGS. 3 and 4A, 4B, and 4C.

In a first step 102, the physician inserts catheter 12 into the patient, and adjusts the position of probe 18 using the signals from sensor 22. The physician adjusts the position of the probe to contact tissue 66 and to be correctly aligned with section 68, so that electrode 62 is able to ablate section 68.

In a second step 104, the physician activates system 10 to begin ablation by setting the system to operate in the ablation mode. On activation, RF ablation signal generator 35 transfers RF energy to electrode 62, at a power that is sufficient for the interaction between the electrode and the tissue to cause ablation, as described above. Typically, system 10 performs the ablation for a period of approximately 2 minutes.

In a third step 106, while ablation is being performed, RF ultrasonic signal generator 37 transfers RF signals to array 58 that cause the array to transmit a set of one or more focused ARFIs towards section 68, as described above. Also as described above, before, during, and/or after transmission of the ARFI set, RF ultrasonic signal generator 37 transfers RF tracking signals to the array causing the array to transmit ultrasonic tracking pulses.

In a fourth step 108, reflections of the ultrasonic tracking pulses are received by array 58 which converts the reflections to electrical signals. Module 32 uses the electrical signals to form a measure of the elasticity of section 68. Using the elasticity, module 32 generates an image of section 68 showing ablated and unablated "66a" regions of the section. The elasticity measurements also enable the degree of ablation of the ablated regions to be measured, and the degree of ablation is also presented on the image.

In a step 110, the physician assesses from the image of section 68 whether the section has been sufficiently ablated, in which case the physician switches system 10 to the non-ablation mode, and flowchart 100 ends. If there has not been sufficient ablation, the flowchart returns to step 104, so that electrode 62 continues to ablate tissue 66. Thus, steps 104, 106, 108, and 110 are performed iteratively until section 68 has been sufficiently ablated.

In an alternative embodiment of the present invention, the physician performs ablations intermittently, typically for the order of 20s-30s, substantially as described above in step 104. Between each ablation system 10 and the physician implement steps 106, 108, and 110, until, as described above for step 110, section 68 has been sufficiently ablated. The physician then sets system 10 to operate in the non-ablation mode, where flowchart 100 does not apply.

FIG. 6 is a schematic diagram of a probe 118, according to an alternative embodiment of the present invention. Apart from the differences described below, the operation of probe 118 is generally similar to that of probe 18 (FIG. 2), and elements indicated by the same reference numerals in both probes 18 and 118 are generally similar in construction and in operation. Unlike probe 18, probe 118 does not comprise sonolucent electrode 62 or its connecting cable 52. Rather, instead of ablating tissue using RF energy which is transferred by the electrode, probe 118 ablates tissue by directing and focusing from an array 158 High Intensity Focused Ultrasound (HIFU), having energy sufficient to cause ablation.

Array 158 is generally similar to array 58, but in addition to being able to perform the four functions of array 58 listed above, array 158 is also able to generate HIFU.

Figure 7:
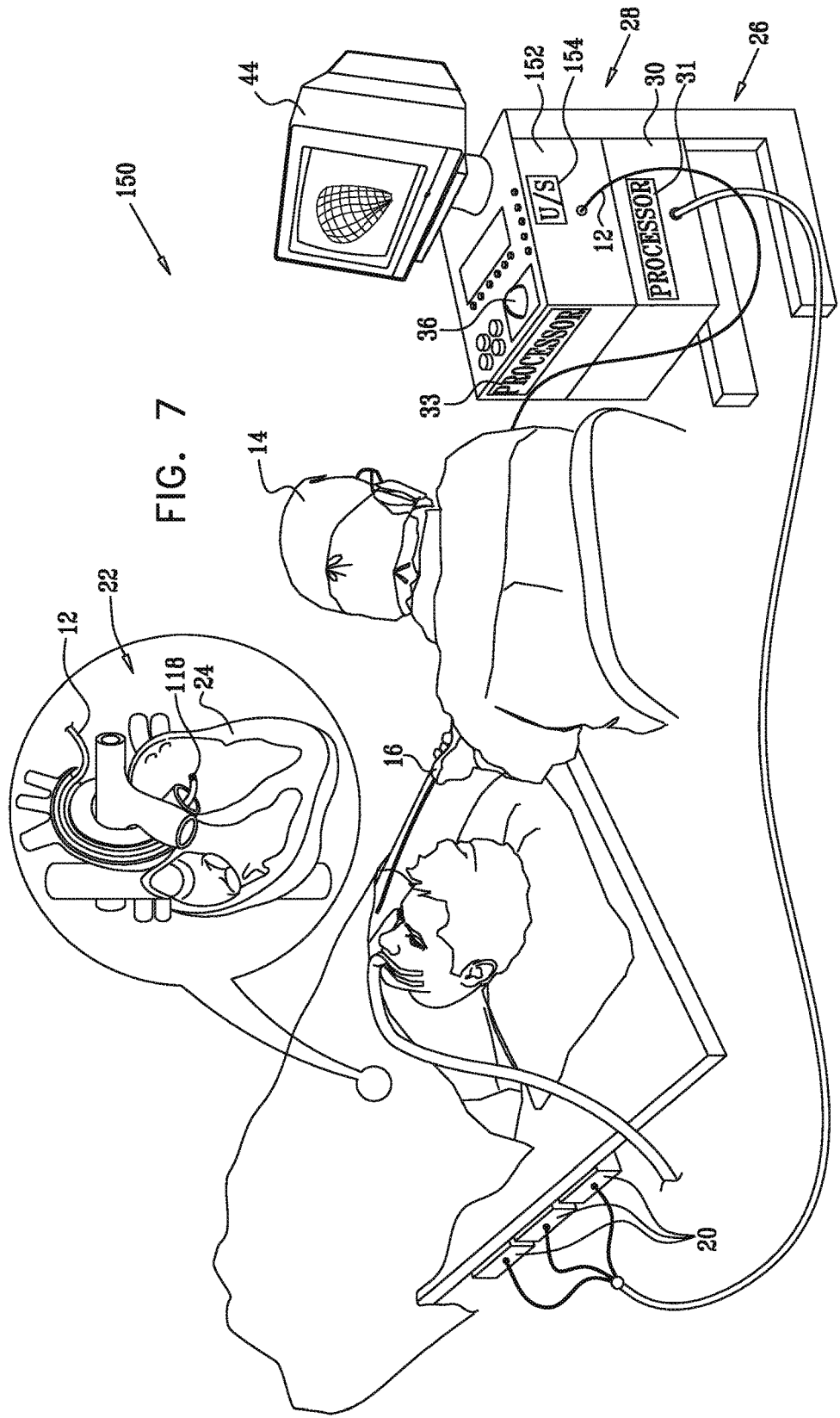
FIG. 7 is a schematic, pictorial illustration of a system for ablating tissue of a patient, according to an alternative embodiment of the present invention.

FIG. 7 is a schematic, pictorial illustration of a system 150 for ablating tissue of a patient, according to an alternative embodiment of the present invention. Apart from the differences described below, the operation of system 150 is generally similar to that of system 10 (FIG. 1), and elements indicated by the same reference numerals in systems 10 and 150 are generally similar in construction and in operation.

In system 150, probe 118 replaces probe 18, and is mounted on the distal end of catheter 12. An ablation transceiver module 152 is generally similar to transceiver module 32. However, since probe 118 does not ablate tissue using RF electrical signals, module 152 does not comprise RF ablation signal generator 35. Instead of RF ultrasonic signal generator 37, module 152 comprises an RF ultrasonic signal generator 154. Thus, processor 33 is able to use generator 154 to provide the four functions listed above for the processor with array 58. In addition, generator 154 is able to generate ultrasound ablating RF signals that cause array 158 to generate HIFU.

As for system 10, system 150 may be configured to operate in an ablation mode or in a non-ablation mode, the two modes being selectable by the physician using device 36. In the ablation mode, system 150 implements a flowchart 200, described below with reference to FIG. 8. In the non-ablation mode, flowchart 200 is not implemented.

FIG. 8 is a flowchart 200 showing steps involved in operating system 150, according to an embodiment of the present invention. Apart from the differences described below, the steps of flowchart 200 are generally similar to those of flowchart 100 (FIG. 5), and procedures of steps indicated by the same reference numerals in flowcharts 100 and 200 are generally similar.

In flowchart 200, instead of step 104, there is a step 202. In step 202, the physician activates system 150 to begin ablation by setting the system to operate in the ablation mode. In the ablation mode processor 33 configures ultrasonic RF signal generator 154 to generate ultrasound ablating RF signals. The ablating RF signals cause array 158 to generate HIFU and thus to ablate tissue 68 (FIG. 6). Typically, the ablation continues for a time of the order of 20s-30s.

Steps 206 and 208 are substantially similar to steps 106 and 108 respectively. However, in flowchart 200, steps 206 and 208 are performed when the ablating signals generated in step 202 have ceased.

It will be understood that, in addition to the functions described above for probes 18, 70, 80, 91, 94, and 118, the probes and the systems to which they are coupled may be used in other ultrasound-based modalities, such as B-mode imaging and/or Doppler imaging. It will also be understood that embodiments of the present invention may be used for ablation, and monitoring of the ablation, for organs other than the heart. Furthermore, ablation processes other than those specifically described herein may be used in embodiments of the present invention. For example, ablation may be performed by implementing substantially any convenient localized change of tissue state, such as may be attained by resistive heating of the tissue. All such ablation processes are assumed to be comprised in the scope of the present invention.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

We claim:

1. A system comprising:
   a probe comprising (i) a position sensor for transmitting signals used to calculate a location and orientation of the probe, (ii) an ablation element which is configured to perform ablation of tissue during an ablation procedure; and (iii) an ultrasonic transducer, which is configured to transmit acoustic radiation force impulses and tracking pulses to the tissue;

wherein the ultrasonic transducer is mounted in acoustic contact with the ablation element such that forward ultrasound waves and returning ultrasonic waves traverse the ablation element and wherein the ultrasonic waves comprise acoustic radiation force impulses, ultrasonic tracking pulses and tracking pulse reflections to monitor the ablation of tissue;

wherein the ablation element comprises an axial aperture spanning from a front surface to a rear surface;

wherein the aperture is filled with acoustically transmissive transmission medium;

wherein said ultrasonic transducer is positioned against the transmission medium;

wherein the aperture through the ablation element has a uniform diameter, and wherein the ultrasonic transducer has a uniform diameter, and wherein the uniform diameter of the aperture and the uniform diameter of the ultrasonic transducer are equal; and wherein the ultrasonic transducer is aligned with the aperture, and is configured to direct the acoustic radiation force impulses axially through the aperture;

the system further comprising:

a display; and a transceiver module comprising (i) a processor, (ii) an RF signal generator configured to generate and transmit RF ablating signals to the ablation element, and (iii) an ultrasonic signal generator configured to generate and transmit signals to the ultrasonic transducer, the processor configured to measure a displacement of the tissue in response to the acoustic radiation force impulses while ablation is being performed on the tissue by the ablation element during the ablation procedure by measuring a time of travel of the tracking pulses using a reflection of the tracking pulses from the tissue so as to monitor the ablation thereof and to calculate elasticity of ablated tissue from unablated tissue using the time of travel of the tracking pulses, the processor of the transceiver module also configured to use the elasticity to generate an image on the display differentially showing ablated tissue and unablated tissue while ablation is being performed on the tissue by the ablation element during the ablation procedure.

2. The system according to claim 1, wherein the ablation element is at a distal tip of the probe;

wherein the ablation element has a front surface oriented axially away from the probe for contacting tissue, and a rear surface facing opposite the front surface.

3. The system according to claim 2:

wherein the rear surface of the ablation element and a rear surface of the transmission medium are coplanar;

wherein the front surface of the ablation element and a front surface of the transmission medium are coplanar;

wherein the transmission medium is uninterrupted from said rear surface of the transmission medium through said front surface of the transmission medium;

wherein the ultrasonic transducer is positioned against the rear surface of the transmission medium.

4. The system according to claim 1, wherein the ultrasonic transducer comprises an array of transducer elements.

5. The system according to claim 4, wherein the array is configured to focus the acoustic radiation force impulses onto the tissue.

6. The system according to claim 4, wherein the array is configured to generate the image of the tissue.

7. The system according to claim 1, wherein the ablation element comprises an electrode configured to perform radio-frequency (RF) ablation of the tissue.

8. The system according to claim 7, wherein the electrode comprises a sonolucent electrode, and wherein the transducer is configured to transmit the acoustic radiation force impulses in response to receipt of electrical radio-frequency (RF) acoustic radiation force impulses signals, to transmit ultrasonic tracking pulses via the sonolucent electrode to the tissue in response to receipt of electrical RF tracking pulses, to receive respective reflections of the ultrasonic tracking pulses from the tissue via the sonolucent electrode, and to generate electrical RF reflection pulses in response to the reflections.

9. The system according to claim 8, and comprising a processor which is configured to convey the electrical RF acoustic radiation force impulses and the electrical RF tracking pulses to the transducer, and to receive the electrical RF reflection pulses from the transducer so as to measure the displacement of the tissue.

10. The system according to claim 1, wherein the ablation element comprises a cooling element configured to perform cryogenic ablation of the tissue.

11. The system according to claim 1, wherein the ablation element comprises a microwave radiator configured to perform microwave ablation of the tissue.

12. The system according to claim 1, and wherein the ultrasonic waves that traverse the ablation element comprise acoustic radiation force impulses, ultrasonic tracking pulses and tracking pulse reflections.

13. The system according to claim 1, and wherein the ultrasonic transducer is in direct contact with the ablation element.

14. The system according to claim 1, and wherein the ultrasonic transducer is separated from the ablation element by an acoustically conductive material.

15. The system according to claim 14 and wherein the acoustically conductive material is a plastic.

16. Apparatus for ablating tissue, comprising:

a probe comprising:

a position sensor for transmitting signals used to calculate a location and orientation of the probe, an array of ultrasonic transducer elements which is configured to direct ultrasonic waves to the tissue in response to an electrical radio-frequency (RF) signal, and to receive reflected ultrasonic waves from the tissue, and an ablation element at a distal tip of the probe which is configured to perform ablation of the tissue during an ablation procedure;

wherein the ultrasonic transducer elements are mounted in acoustic contact with the ablation element such that forward ultrasound waves and returning ultrasonic waves generated by the ultrasonic transducer elements traverse the ablation element and wherein the ultrasonic waves comprise acoustic radiation force impulses, ultrasonic tracking pulses and tracking pulse reflections to monitor the ablation of tissue;

wherein the ablation element comprises an axial aperture spanning from a front surface to a rear surface;

wherein the aperture is filled with acoustically transmissive transmission medium;

wherein said ultrasonic transducer is positioned against the transmission medium;

wherein the aperture through the ablation element has a uniform diameter, and wherein the ultrasonic transducer has a uniform diameter, and wherein the uniform diameter of the aperture and the uniform diameter of the ultrasonic transducer are equal; and wherein the ultrasonic transducer is aligned with the aperture, and is configured to direct the acoustic radiation force impulses axially through the aperture;

the probe further comprising:

a display; and an RF transceiver comprising (i) a processor, (ii) an RF signal generator configured to generate and transmit RF ablating signals to the ablation element, and (iii) an ultrasonic signal generator configured to generate and transmit signals to the ultrasonic transducer, the processor configured wherein:

in a first transceiver state is configured to cause the RF signal generator signal generator to convey an electrical ablating RF signal to the array causing the array to transmit ablation ultrasonic pulses to the tissue, the ablation ultrasonic pulses having an energy sufficient to cause ablation of the tissue, in a second transceiver state is configured to convey an electrical acoustic radiation force impulse RF signal to the array causing the array to transmit an acoustic radiation force impulse to the tissue, and in a third transceiver state is configured:

to cause the ultrasonic signal generator to convey an electrical tracking RF signal to the array causing the array to transmit one or more tracking ultrasonic pulses to the tissue, to receive electrical RF reflection signals from the array generated in response to the array receiving reflections of the one or more tracking ultrasonic pulses from the tissue, and to measure a displacement of the tissue in response to the electrical RF reflection signals while ablation is being performed by the ablation element on the tissue during the ablation procedure by measuring a time of travel of the one or more tracking ultrasonic pulses using a reflection of the one or more tracking ultrasonic pulses from the tissue, so as to monitor the ablation of the tissue and to calculate elasticity of ablated tissue from unablated tissue using the time of travel of the one or more tracking ultrasonic pulses, and in a fourth transceiver state is configured:

to convey an electrical imaging RF signal to the array causing the array to transmit one or more imaging ultrasonic pulses to the tissue, and to receive electrical RF imaging reflection signals from the array generated in response to the array receiving reflections of the one or more imaging ultrasonic pulses from the tissue and to use the elasticity to generate an image on the display showing ablated tissue from unablated tissue while ablation is being performed by the ablation element on the tissue during the ablation procedure.

17. The probe according to claim 16, and wherein the ultrasonic waves that traverse the ablation element comprise acoustic radiation force impulses, ultrasonic tracking pulses and tracking pulse reflections.

18. The probe according to claim 16, and wherein the ultrasonic transducer elements are in direct contact with the ablation element.

19. The probe according to claim 16, and wherein the ultrasonic transducer elements are separated from the ablation element by an acoustically conductive material.

20. The probe according to claim 19 and wherein the acoustically conductive material is a plastic.

21. A method for ablating tissue, comprising:

providing a probe comprising a position sensor for transmitting signals used to calculate a location and orientation of the probe and an ablation element which is configured to perform ablation of tissue during an ablation procedure;

the method further comprising:

providing a transceiver comprising (i) a processor, (ii) an RF signal generator configured to generate and transmit RF ablating signals to the ablation element, and (iii) an ultrasonic signal generator configured to generate and transmit signals to the ultrasonic transducer;

positioning the far end of the probe substantially in contact with tissue based on the location and orientation of the probe;

performing ablation of the tissue using the ablation element from RF ablating signals generated and transmitted to the ablation element;

providing an ultrasonic transducer in acoustic contact with the ablation element such that forward ultrasonic waves and returning ultrasonic waves generated by the ultrasonic transducer traverse the ablation element and and wherein the ultrasonic waves comprise acoustic radiation force impulses, ultrasonic tracking pulses and tracking pulse reflections used to monitor the ablation of tissue;

providing an axial aperture in the ablation element spanning from a front surface to a rear surface;

wherein the aperture through the ablation element has a uniform diameter, and wherein the ultrasonic transducer has a uniform diameter, and wherein the uniform diameter of the aperture and the uniform diameter of the ultrasonic transducer are equal; and wherein the ultrasonic transducer is aligned with the aperture, and is configured to direct the acoustic radiation force impulses axially through the aperture;

transmitting one or more tracking ultrasonic pulses to the tissue using the ultrasonic signal generator;

transmitting acoustic radiation force impulses from the transducer to the tissue through the transmission medium; and using the processor for measuring a displacement of the tissue in response to the acoustic radiation force impulses while ablation is being performed on the tissue by the ablation element during the ablation procedure by measuring a time of travel of the one or more tracking ultrasonic pulses using a reflection of the one or more tracking ultrasonic pulses from the tissue so as to monitor the ablation thereof;

calculating the elasticity of ablated tissue from unablated tissue using the time of travel of the one or more tracking ultrasonic pulses; and using the elasticity to generate an image on a display showing ablated tissue from unablated tissue while ablation is being performed on the tissue by the ablation element during the ablation procedure.

22. The method according to claim 21, wherein the ablation element has a front surface oriented axially away from the probe for contacting tissue, and a rear surface facing opposite the front surface;

wherein the rear surface of the ablation element and a rear surface of the transmission medium are coplanar;

wherein the front surface of the ablation element and a front surface of the transmission medium are coplanar;

wherein an ultrasonic transducer is positioned against the rear surface of the transmission medium;

wherein the transmission medium provides a continuous path from the ultrasonic transducer to a far end of the probe;

wherein the ultrasonic transducer has a diameter, the aperture of the ablation element has a diameter, said diameters being substantially the same;

wherein the ultrasonic transducer is aligned with the aperture; and the method further comprising: using the ultrasonic transducer, directing acoustic radiation force impulses into the tissue through the aperture.

23. The method according to claim 22,
wherein the transmission medium comprises silicone;
the method comprising positioning the front surface of the transmission medium against the tissue, and directing acoustic radiation force impulses through the transmission medium in the tissue.

24. The method according to claim 21, wherein the ultrasonic transducer comprises an array of transducer elements.

25. The method according to claim 24, and comprising configuring the array to focus the acoustic radiation force impulses onto the tissue.

26. The method according to claim 24, and comprising configuring the array to generate the image of the tissue.

27. The method according to claim 21, wherein the ablation element comprises an electrode configured to perform radio-frequency (RF) ablation of the tissue.

28. The method according to claim 27, wherein the electrode comprises a sonolucent electrode, and wherein the transducer is configured to transmit the acoustic radiation force impulses in response to receipt of electrical radio-frequency (RF) acoustic radiation force impulse signals, to transmit ultrasonic tracking pulses via the sonolucent electrode to the tissue in response to receipt of electrical RF tracking pulses, to receive respective reflections of the ultrasonic tracking pulses from the tissue via the sonolucent electrode, and to generate electrical RF reflection pulses in response to the respective reflections.

29. The method according to claim 21, wherein the ablation element comprises a cooling element configured to perform cryogenic ablation of the tissue.

30. The method according to claim 21, wherein the ablation element comprises a microwave radiator configured to perform microwave ablation of the tissue.

31. The method according to claim 21, and wherein the ultrasonic waves that traverse the ablation element comprise acoustic radiation force impulses, ultrasonic tracking pulses and tracking pulse reflections.

32. The method according to claim 21, and wherein the ultrasonic transducer is in direct contact with the ablation element.

33. The method according to claim 21, and wherein the ultrasonic transducer is separated from the ablation element by an acoustically conductive material.

34. The method according to claim 33 and wherein the acoustically conductive material is a plastic.

35. A method for ablating tissue, comprising:
providing a probe comprising:
a position sensor for transmitting signals used to calculate a location and orientation of the probe,
an ablation element which is configured to perform ablation of tissue during an ablation procedure, wherein the ablation element has a front surface oriented axially away from the probe for contacting tissue, a rear surface facing opposite the front surface, and an axial aperture from the front surface to the rear surface;

wherein the ablation element comprises an axial aperture spanning from a front surface to a rear surface; and an array of ultrasonic transducer elements to direct ultrasonic waves to the tissue in response to an electrical radio-frequency (RF) signal, and to receive reflected ultrasonic waves from the tissue;

wherein the aperture through the ablation element has a uniform diameter and wherein the ultrasonic transducer has a diameter, and wherein the aperture and ultrasonic transducer have equal diameters, and wherein the ultrasonic transducer is aligned with the aperture and configured to direct the acoustic radiation force impulses axially through the aperture;

wherein the ultrasonic transducer elements are mounted in acoustic contact with the ablation element such that forward ultrasound waves and returning ultrasonic waves traverse the ablation element and wherein the ultrasonic waves comprise acoustic radiation force impulses, ultrasonic tracking pulses and tracking pulse reflections to monitor the ablation of tissue;

providing an RF transceiver comprising (i) a processor, (ii) an RF signal generator configured to generate and transmit RF ablating signals to the ablation element, and (iii) an ultrasonic signal generator configured to generate and transmit signals to the ultrasonic transducer;

positioning the probe substantially in contact with tissue based on the location and orientation of the probe;

the RF transceiver configured to operate in a first transceiver state to cause the RF signal generator signal generator to convey an electrical ablating RF signal to the array causing the array to transmit ablation ultrasonic pulses to the tissue, the ablation ultrasonic pulses having an energy sufficient to cause ablation of the tissue, and configured to operate in a second transceiver state to convey an electrical acoustic radiation force impulse RF signal to the array causing the array to transmit an acoustic radiation force impulse to the tissue, and in a third transceiver state is configured cause the ultrasonic signal generator to:

to convey an electrical tracking RF signal to the array causing the array to transmit one or more tracking ultrasonic pulses to the tissue, to receive electrical RF reflection signals from the array generated in response to the array receiving reflections of the one or more tracking ultrasonic pulses from the tissue, and to measure a displacement of the tissue in response to the electrical RF reflection signals while ablation is being performed on the tissue by the ablation element during the ablation procedure by measuring a time of travel of the one or more tracking ultrasonic pulses using a reflection of the one or more tracking ultrasonic pulses from the tissue, so as to monitor the ablation of the tissue and to calculate the elasticity ablated tissue from unablated tissue using the time of travel of the one or more tracking ultrasonic pulses, and in a fourth transceiver state is configured to convey an electrical imaging RF signal to the array causing the array to transmit one or more imaging ultrasonic pulses to the tissue, and to receive electrical RF imaging reflection signals from the array generated in response to the array receiving reflections of the one or more imaging ultrasonic pulses from the tissue and using the elasticity to generate an image on a display showing ablated tissue from unablated tissue while ablation is being performed on the tissue by the ablation element during the ablation procedure.

* * * * *